(12) United States Patent
Matsuda et al.

(10) Patent No.: US 6,762,037 B1
(45) Date of Patent: Jul. 13, 2004

(54) PROCESS FOR PRODUCING COENZYME Q10

(75) Inventors: Hideyuki Matsuda, Matsue (JP); Makoto Kawamukai, Matsue (JP); Kazuyoshi Yajima, Akashi (JP); Yasuhiro Ikenaka, Kobe (JP); Junzo Hasegawa, Akashi (JP); Satomi Takahashi, Kobe (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/830,111

(22) PCT Filed: Aug. 24, 2000

(86) PCT No.: PCT/JP00/05659

§ 371 (c)(1),
(2), (4) Date: Jul. 23, 2001

(87) PCT Pub. No.: WO01/14567

PCT Pub. Date: Mar. 1, 2001

(30) Foreign Application Priority Data

Aug. 24, 1999 (JP) .......................................... 11-237561

(51) Int. Cl.⁷ .......................... C12P 21/02; C12N 1/21; C12N 9/10; C12N 15/52; C07H 21/04
(52) U.S. Cl. ........................ 435/68.1; 435/41; 435/193; 435/252.3; 435/252.33; 435/254.11; 435/320.1; 536/23.2
(58) Field of Search ........................ 435/41, 68.1, 193, 435/252.3, 252.33, 254.11, 320.1; 536/23.2

(56) References Cited

U.S. PATENT DOCUMENTS 6,103,488 A   8/2000 Matsuda et al. .............. 435/41

FOREIGN PATENT DOCUMENTS

EP   1 070 759 A1   1/2001

OTHER PUBLICATIONS

Goto et al, *J. Gen. Appl. Microbiol. 33*: 75–85 (1987).
Okada et al, *Eur. J. Biochem. 255*, 52–59 (1998).
Suzuki et al. Journal of Biochemistry, (Mar. 1997) 121 (3) 496–505.*

* cited by examiner

*Primary Examiner*—Elizabeth Slobodyansky
(74) *Attorney, Agent, or Firm*—Connolly Bove Lodge & Hutz LLP

(57) ABSTRACT

The present invention has for its object to isolate a gene coding for the enzyme synthesizing the coenzyme $Q_{10}$ side chain from a fungal strain of the genus Saitoella and exploit it to advantage for the efficient microbial production of coenzyme $Q_{10}$.

The present invention provides;
  a DNA having the nucleotide sequence shown under SEQ ID NO:1
  a DNA having a nucleotide sequence derived from the nucleotide sequence of SEQ ID NO:1 by the deletion, addition, insertion and/or substitution of one or a plurality of nucleotides
  and coding for a protein having decaprenyl diphosphate synthase activity
  a DNA which hybridizes with the DNA having the nucleotide sequence of SEQ ID NO:1 under a stringent condition
  and codes for a protein having decaprenyl diphosphate synthase activity.

16 Claims, 3 Drawing Sheets

E. Coli DH5 α

E. Coli DH5 α / pNTSa1

CoQ10 Standard

SEQUENCE LISTING

<160> NUMBER OF SEQ ID NOS: 9

<210> SEQ ID NO 1
<211> LENGTH: 1653
<212> TYPE: DNA
<213> ORGANISM: Saioella complicata

<400> SEQUENCE: 1

```
ttttgtgggg tcgaaaagtc ggcacgggtg caggttcggc ttgagaccag taaaggctcg      60
gagattgagt tcaggacaaa gctttgatcc gtgaggtcta catcttcagc aaatcatttc     120
aaatccatat accatggcct caccagcact gcggatacga agcatcagct ctcgatcaat     180
cgcctctctg cgatcggtta ccctaagaac agcctcggca ccttcattac gactaagatg     240
taccccgacg agccggccat cgagttcatg ggctgctgct gtgtcttcgg cgtcgagact     300
ggttgagcct gatccgaatc aacctctcat caatccgctc aacttggtcg gtcccgagat     360
gtcaaatctt acatccaaca tccgatctct cctcggttca ggacaccctt ctctcgacac     420
tgtcgctaaa tactatgttc agtctgaggg aaagcatatt cgtccgctca tggtactgct     480
```

-continued

```
gatggctcag gcgacggagg ttgcgccaaa agttcagggt tgggagaagg tcgtggaggt    540
tccggtgaac gagggactcg caccaccaga ggtgctcaat gacaagaacc cagatatgat    600
gaacatgagg tcaggaccat taacgaagga cggcgagatc gagggacaga cgtcgaatat    660
cctcgcctcg caacggcggt tggctgagat cacggagatg atccatgcag catcactcct    720
ccacgacgca gttatcgacg cttccgagac cagacgaaac gcaccatccg gaaaccaggc    780
attcggaaac aagatggcga ttttggctgg tgatttcttg ttgggacggg cgtctgttgc    840
attggcgagg ttgcgcaatc cggaggtgat tgagcttttg gctactgtta ttgcaaactt    900
ggttgaggga gagttcatgc agttgaaaaa tactgttgat gatgcgattg aggctacggc    960
gacgcaggaa acgttcgatt actatttgca gaagacttac ttgaagactg cgtccttgat   1020
tgccaagtcg tgcagagcaa gtcgcttct gggtggtgct acgcctgagg ttgctgatgc   1080
tgcttatgct tacggaagga accttggttt ggcattccag atcgtcgacg acatgctcga   1140
ctacaccgtc tccgctaccg acctcggtaa gcccgccggt gcagacctcc agctcggtct   1200
cgccaccgcg ccggccctct tcgcatggaa gcaccacgcc gagctcggtc ccatgatcaa   1260
gcgcaagttc tctgacccag agacgtcga gcgtgcacgc gagttggtcg agaaaagtga   1320
tggattggag aagacgagag ccttggcgga ggagtatgcc cagaaggcgt tggatgcaat   1380
tcggacgttc ccggagagtc cggcacggaa ggctttggag cagttgacgg acaaggtgtt   1440
gactaggtca agataggaat tcgagctcgg tacccgggga tcctctagag tcgacctgca   1500
ggcatgcaag cttggctgtt ttggcggatg agagaagatt ttcagcctga tacagattaa   1560
atcagaacgc agaagcggtc tgataaaaca gaatttgcct ggcggcagta gcgcggtggt   1620
cccacctgac cccatgccga actcagaagt gaa                                1653
```

<210> SEQ ID NO 2
<211> LENGTH: 446
<212> TYPE: PRT
<213> ORGANISM: Saitoella complicata

<400> SEQUENCE: 2

```
Ser Glu Gln Ile Asp Asn Met Ala Ser Pro Ala Leu Arg Ile Arg Ser
  1               5                  10                  15

Ile Ser Ser Arg Ser Ile Ala Ser Leu Arg Ser Val Thr Leu Arg Thr
             20                  25                  30

Ala Ser Ala Pro Ser Leu Arg Leu Arg Cys Thr Pro Thr Ser Arg Pro
         35                  40                  45

Ser Ser Ser Trp Ala Ala Ala Val Ser Ser Ala Ser Arg Leu Val Glu
     50                  55                  60

Pro Asp Pro Asn Gln Pro Leu Ile Asn Pro Leu Asn Leu Val Gly Pro
 65                  70                  75                  80

Glu Met Ser Asn Leu Thr Ser Asn Ile Arg Ser Leu Leu Gly Ser Gly
                 85                  90                  95

His Pro Ser Leu Asp Thr Val Ala Lys Tyr Tyr Val Gln Ser Glu Gly
            100                 105                 110

Lys His Ile Arg Pro Leu Met Val Leu Leu Met Ala Gln Ala Thr Glu
        115                 120                 125

Val Ala Pro Lys Val Gln Gly Trp Glu Lys Val Glu Val Pro Val
    130                 135                 140

Asn Glu Gly Leu Ala Pro Pro Glu Val Leu Asn Asp Lys Asn Pro Asp
145                 150                 155                 160
```

-continued

```
Met Met Asn Met Arg Ser Gly Pro Leu Thr Lys Asp Gly Glu Ile Glu
            165                 170                 175
Gly Gln Thr Ser Asn Ile Leu Ala Ser Gln Arg Arg Leu Ala Glu Ile
            180                 185                 190
Thr Glu Met Ile His Ala Ala Ser Leu Leu His Asp Asp Val Ile Asp
            195                 200                 205
Ala Ser Glu Thr Arg Arg Asn Ala Pro Ser Gly Asn Gln Ala Phe Gly
210                 215                 220
Asn Lys Met Ala Ile Leu Ala Gly Asp Phe Leu Leu Gly Arg Ala Ser
225                 230                 235                 240
Val Ala Leu Ala Arg Leu Arg Asn Pro Glu Val Ile Glu Leu Leu Ala
            245                 250                 255
Thr Val Ile Ala Asn Leu Val Glu Gly Glu Phe Met Gln Leu Lys Asn
            260                 265                 270
Thr Val Asp Asp Ala Ile Glu Ala Thr Ala Thr Gln Glu Thr Phe Asp
            275                 280                 285
Tyr Tyr Leu Gln Lys Thr Tyr Leu Lys Thr Ala Ser Leu Ile Ala Lys
            290                 295                 300
Ser Cys Arg Ala Ser Ala Leu Leu Gly Gly Ala Thr Pro Glu Val Ala
305                 310                 315                 320
Asp Ala Ala Tyr Ala Tyr Gly Arg Asn Leu Gly Leu Ala Phe Gln Ile
                325                 330                 335
Val Asp Asp Met Leu Asp Tyr Thr Val Ser Ala Thr Asp Leu Gly Lys
            340                 345                 350
Pro Ala Gly Ala Asp Leu Gln Leu Gly Leu Ala Thr Ala Pro Ala Leu
            355                 360                 365
Phe Ala Trp Lys His His Ala Glu Leu Gly Pro Met Ile Lys Arg Lys
            370                 375                 380
Phe Ser Asp Pro Gly Asp Val Glu Arg Ala Arg Glu Leu Val Glu Lys
385                 390                 395                 400
Ser Asp Gly Leu Glu Lys Thr Arg Ala Leu Ala Glu Glu Tyr Ala Gln
                405                 410                 415
Lys Ala Leu Asp Ala Ile Arg Thr Phe Pro Glu Ser Pro Ala Arg Lys
            420                 425                 430
Ala Leu Glu Gln Leu Thr Asp Lys Val Leu Thr Arg Ser Arg
            435                 440                 445
```

<210> SEQ ID NO 3
<211> LENGTH: 24
<212> TYPE: DNA
<213> ORGANISM: Artificial Sequence
<220> FEATURE:
<223> OTHER INFORMATION: Primer DPS-1
<220> FEATURE:
<221> NAME/KEY: misc_feature
<222> LOCATION: (10)..(10)
<223> OTHER INFORMATION: n stands for g, a, t, or c
<220> FEATURE:
<221> NAME/KEY: misc_feature
<222> LOCATION: (13)..(13)
<223> OTHER INFORMATION: n stands for g, a, t, or c

<400> SEQUENCE: 3
aaggatcctn ytncaygayg aygt                24

<210> SEQ ID NO 4
<211> LENGTH: 17
<212> TYPE: DNA
<213> ORGANISM: Artificial Sequence

```
<220> FEATURE:
<223> OTHER INFORMATION: Primer DPS-1 1AS
<220> FEATURE:
<221> NAME/KEY: misc_feature
<222> LOCATION: (6)..(6)
<223> OTHER INFORMATION: n stands for g, a, t, or c
<220> FEATURE:
<221> NAME/KEY: misc_feature
<222> LOCATION: (15)..(15)
<223> OTHER INFORMATION: n stands for g, a, t, or c

<400> SEQUENCE: 4
arytgnadra aytcncc                                                17

<210> SEQ ID NO 5
<211> LENGTH: 21
<212> TYPE: DNA
<213> ORGANISM: Artificial Sequence
<220> FEATURE:
<223> OTHER INFORMATION: Primer Sa-1S

<400> SEQUENCE: 5
gagaccagac gaaacgcacc a                                           21

<210> SEQ ID NO 6
<211> LENGTH: 21
<212> TYPE: DNA
<213> ORGANISM: Artificial Sequence
<220> FEATURE:
<223> OTHER INFORMATION: Primer Sa-2AS

<400> SEQUENCE: 6
tggtgcgttt cgtctggtct c                                           21

<210> SEQ ID NO 7
<211> LENGTH: 26
<212> TYPE: DNA
<213> ORGANISM: Artificial Sequence
<220> FEATURE:
<223> OTHER INFORMATION: Primer Sa-N1

<400> SEQUENCE: 7
aacatatggc ctcaccagca ctgcgg                                      26

<210> SEQ ID NO 8
<211> LENGTH: 29
<212> TYPE: DNA
<213> ORGANISM: Artificial Sequence
<220> FEATURE:
<223> OTHER INFORMATION: Primer Sa-C

<400> SEQUENCE: 8
aagaattcct atcttgacct agtcaacac                                   29

<210> SEQ ID NO 9
<211> LENGTH: 8
<212> TYPE: PRT
<213> ORGANISM: Saitoella complicata

<400> SEQUENCE: 9

Gly Asp Phe Leu Leu Gly Arg Ala
1               5
```

PROCESS FOR PRODUCING COENZYME Q10

TECHNICAL FIELD

The present invention relates to a process for producing a coenzyme $Q_{10}$ for pharmaceutical and other uses. More particularly, the invention relates to a process for producing coenzyme $Q_{10}$ which comprises isolating a gene coding for the coenzyme $Q_{10}$ side-chain synthase, which is a key enzyme involved in the biosynthesis of coenzyme $Q_{10}$, i.e. decaprenyl diphosphate synthase, from a fungal strain of the genus Saitoella and introducing it into a host microorganism to let it elaborate coenzyme $Q_{10}$.

BACKGROUND ART

The conventional technology for commercial production of coenzyme $Q_{10}$ comprises isolating the coenzyme from a tobacco or other plant and modifying the length of its side chain by a synthetic technique.

While it is known that coenzyme $Q_{10}$ is produced by a broad spectrum of organisms ranging from microorganisms, such as bacteria and yeasts, to higher animals and plants, the method comprising culturing a microorganism and extracting coenzyme $Q_{10}$ from the microorganism is regarded as one of the most effective production methods and has actually been exploited commercially. However, the prior art methods are invariably poor in productivity, providing for only low outputs and/or involving time-consuming procedures.

The pathways for biosynthesis of coenzyme $Q_{10}$ in organisms are partly different between the prokaryote and the eukaryote but invariably comprise a complicated cascade of reactions involving many kinds of enzymes. However, these pathways are basically comprised of three fundamental steps, namely the step of synthesizing decaprenyl diphosphate as the precursor of the prenyl side-chain of coenzyme $Q_{10}$, the step of synthesizing p-hydroxybenzoic acid as the basis of the quinone ring of coenzyme $Q_{10}$, and the step of coupling these two compounds together and effecting a serial substituent transformation to complete coenzyme $Q_{10}$. Of these reactions, the reaction determinant of the length of the side-chain of coenzyme $Q_{10}$ and acknowledged to be the rate-determining step of its biosynthesis, i.e. the reaction catalyzed by decaprenyl diphosphate synthase, is considered to be the most important reaction. Therefore, in order that coenzyme $Q_{10}$ may be produced with good efficiency, it seems worthwhile to isolate the key gene involved in said biosynthesis, namely the gene coding for decaprenyl diphosphate synthase, and utilize it for enhanced production of the enzyme. As sources of the gene, fungi capable of producing coenzyme $Q_{10}$ in comparatively large amounts can be regarded as useful candidates.

Heretofore, genes coding for decaprenyl diphosphate synthase have been isolated from several kinds of microorganisms, such as Schizosacch aromyces pombe (JP09-173076A) and Gluconobacter suboxydans (JP10-57072A), etc., but the inherent coenzyme $Q_{10}$ productivity of these micrcorganisms cannot be considered high enough and neither an efficient cultural protocol for these microorganisms nor an efficient isolation and purification procedure has been established as yet. Therefore, there has been a standing demand for isolation of a coenzyme $Q_{10}$-encoding gene from a microorganism capable of highly producing a coenzyme $Q_{10}$.

Devoted to providing a solution to the above-mentioned production problems, the present invention has for its object to isolate a gene coding for the enzyme synthesizing the coenzyme $Q_{10}$ side chain from a fungal strain of the genus Saitoella and exploit it to advantage for the efficient microbial production of coenzyme $Q_{10}$.

DISCLOSURE OF THE INVENTION

To accomplish the above object, in the present invention, the key gene involved in the biosynthesis of coenzyme $Q_{10}$, namely the gene coding for decaprenyl diphosphate synthase, was isolated from a fungal strain of the genus Saitoella in the first place. Then, this gene was introduced and allowed to be expressed in a host microorganism, such as Escherichia coli, to thereby enable the host to produce coenzyme $Q_{10}$ with efficiency.

The inventors of the present invention made intensive investigations for isolating such genes coding for decaprenyl diphosphate synthase from fungal strains of the genus Saitoella capable of producing comparatively large amounts of coenzyme $Q_{10}$ and have succeeded in isolating said genes.

The present invention, therefore, is concerned with a DNA of the following (a), (b) or (c).

(a) a DNA having the nucleotide sequence shown under SEQ ID NO:1
(b) a DNA having a nucleotide sequence derived from the nucleotide sequence of SEQ ID NO:1 by the deletion, addition, insertion and/or substitution of one or a plurality of nucleotides
and coding for a protein having decaprenyl diphosphate synthase activity
(c) a DNA which hybridizes with the DNA having the nucleotide sequence of SEQ ID NO:1 under a stringent condition and codes for a protein having decaprenyl diphosphate synthase activity.

The present invention is further concerned with a protein of the following (d) or (e).

(d) a protein having the amino acid sequence shown under SEQ ID NO:2
(e) a protein having an amino acid sequence derived from the amino acid sequence of SEQ ID NO:2 by the deletion, addition, insertion and/or substitution of one or a plurality of amino acids
and having decaprenyl diphosphate synthase activity.

The invention is further concerned with a DNA coding for this protein.

The present invention is further concerned with an expression vector containing said DNA. For the expression vector of the invention, various vector systems heretofore known can be utilized and, therefore, may for example be pNTSal as constructed by cloning the DNA having the sequence of SEQ ID NO:1 into the vector pUCNT for expression.

The present invention is further concerned with a transformant as constructed by transforming a host microorganism with said DNA. As the host microorganism for the invention, Escherichia coli can be used with advantage.

The invention is further concerned with a process for producing coenzyme $Q_{10}$
which comprises culturing said transformant in a culture broth and harvesting the coenzyme $Q_{10}$ produced and accumulated in the resulting culture. The host microorganism for this process is not particularly restricted but may be Escherichia coli to mention a preferred example. The coenzyme Q produced by Escherichia coli is coenzyme $Q_8$ but the invention enables this microorganism to produce coenzyme $Q_{10}$.

The inventors made intensive investigations on the isolation of the enzyme gene from a fungal strain which belongs to the genus Saitoella and is capable of producing comparatively large amounts of coenzyme $Q_{10}$ and succeeded in acquiring a fragment of the particular gene by a PCR technique.

The inventors compared the sequence of the known gene coding for decaprenyl diphosphate synthase with the genes cording for polyprenyl diphosphate synthases, namely long-chain prenyl synthases which are analogous to said known enzyme gene but differ from the same in chain length and, for the region of high homology, synthesized various PCR primers. Using these primers in various combinations, they studied PCR conditions. As a result, they found by analysis of the gene sequence that when a PCR using DPS-1 (SEQ ID NO:3) and DPS-1 1AS (SEQ ID NO:4) as primers is carried out according to the protocol of heat-treatment at 94° C.×3 minutes, followed by 40 cycles of 94° C., 1 minute→43° C., 2 min→72° C., 2 minutes, a ca 220 bp fragment of the enzyme gene can be amplified from the chromosome gene of *Saitoella complicata* IFO 10748, a fungus belonging to the genus Saitoella.

Then, to acquire the full length of this enzyme gene, the chromosome gene *Saitoella complicata* IFO 10748 is digested with the restriction enzyme EcoRI and inserted into a λ phage vector to construct a recombinant phage library. After the plaque is transferred to a nylon membrane, the plaque hybridization is carried out using the labeled PCR fragment, whereby a clone having the full-length decaprenyl diphosphate synthase gene can be obtained.

Sequencing of the decaprenyl diphosphate synthase gene occurring in the above clone reveals that the gene has the nucleotide sequence shown under SEQ ID NO:1 of SEQUENCE LISTING. The amino acid sequence deduced from the above nucleotide sequence is shown under SEQ ID NO:2. Here, a sequence characteristic of a gene coding for decaprenyl diphosphate synthase is observed.

The DNA of the invention may be any of the DNA having the nucleotide sequence shown under SEQ ID NO:1, the DNA having a nucleotide sequence derived from the sequence of SEQ ID NO:1 by the deletion, addition, insertion and/or substitution of one or a plurality of nucleotides and coding for a protein having decaprenyl diphosphate synthase activity, and the DNA which hybridizes with the DNA having the nucleotide sequence of SEQ ID NO:1 under a stringent condition and codes for a protein having decaprenyl diphosphate synthase activity.

The "nucleotide sequence derived by the deletion, addition, insertion and/or substitution of one or a plurality of nucleotides" means any nucleotide sequence derived by the deletion, addition, insertion and/or substitution of a number of nucleotides of the order which can be deleted, added, inserted and/or substituted by the methods well known in the art, for example as described in, inter alia, Protein, Nucleic Acid, Enzyme, Supplemental Issue: Gene Amplification PCR Technology TAKKAJ 35 (17), 2951–3178 (1990) and Henry A. Erlich (ed.), PCR Technology (the translation edited by Ikunoshin Kato) (1990).

As used in this specification, the term "protein having decaprenyl diphosphate synthase activity" means a protein capable of synthesizing decaprenyl diphosphate in a yield of not less than 10%, preferably not less than 40%, more preferably not less than 60%, still more preferably not less than 80%, relative to the protein having the amino acid sequence shown under SEQ ID NO:2. Such yield measurements can be made by the technique which comprises reacting FDP (farnesyl diphosphate) and $^{14}C$-IPP (radiolabeled isopentenyl diphosphate) with the enzyme of interest, hydrolyzing the resulting $^{14}C$-DPP (decaprenyl diphosphate) with phosphatase, fractionating the hydrolysate by TLC, and assaying the amounts taken up in spots corresponding to the respective chain lengths (Okada et al., Eur. J. Biochem., 255, 55 to 59).

The "DNA which hybridizes with the DNA having the nucleotide sequence of SEQ ID NO:1 under a stringent condition" means a DNA obtained by colony hybridization, plaque hybridization, Southern hybridization or the like hybridization technique using the DNA having the nucleotide sequence of SEQ ID NO:1 as the probe. Anyone skilled in the art may easily acquire the objective DNA by carrying out said hybridization according to the methods described in Molecular Cloning, 2nd Edition (Cold Spring Harbor Laboratory Press, 1989).

The protein of the present invention may have the amino acid sequence shown under SEQ ID NO:2 or an amino acid sequence derived from the amino acid sequence shown under SEQ ID NO:2 by the deletion, addition, insertion and/or substitution of one or a plurality of amino acids and having decaprenyl diphosphate synthase activity.

"The amino acid sequence derived by the deletion, addition, insertion and/or substitution of one or a plurality of amino acids" can be obtained by effecting such deletion, addition, insertion and/or substitution by the technology well known in the art, such as a region-specific mutagenesis technique. Specific procedures are described in Nucleic Acid Res. 10, 6487 (1982), Methods in Enzymology, 100, 448 (1983) and other literature.

The protein of the present invention preferably has an amino acid sequence showing a homology of not less than 60%, preferably not less than 70%, more preferably not less than 80%, still more preferably not less than 90% further still more preferably not less than 95%, to the amino acid sequence shown under SEQ ID NO:2.

The "homology" is calculated by aligning two nucleotide sequences to be compared in the optimum format, counting the matched base positions (A, T, C, G, U or I) between the two sequences, dividing the count by the total number of bases compared, and multiplying the product by 100. Specifically, this calculation can be made using an analytical software such as Hitachi Soft Engineering's DNASIS, Software Development's GENETYX, or Finland CSC's Clustal X, for instance.

While the gene coding for decaprenyl diphosphate synthase must be ligated downstream of a suitable promoter for expression, an expression vector can be constructed, for example by excising a DNA fragment containing the gene with a restriction enzyme or amplifying the enzyme-encoding gene selectively by PCR, followed by cloning it into a vector having a promoter. In the present invention, the expression vector into which the DNA coding for the protein having decaprenyl diphosphate synthase activity may be inserted is not particularly restricted but may for example be one constructed by ligating a suitable promoter to a plasmid derived from *E. coli*. The plasmid of *E. coli* origin includes pBR322, pBR325, pUC19 and pUC119, while the promoter includes T7 promoter, trp promoter, tac promoter, lac promoter and λPL promoter. Further, as the expression vector of this invention, pGEX-2T, pGEX-3T, pGEX-3X (all from Pharmacia), pBluescript, pUC19 (from Toyobo), pMALC2, pET-3T and pUCNT (described in WO 94/03613), etc. can also be mentioned. Among these, pUCNT can be used with advantage. To mention a specific example, the vector pNT-Sal for the expression of a decaprenyl diphosphate synthase gene can be constructed by inserting the gene having the DNA sequence shown under SEQ ID NO:1 into the expression vector pUCNT.

Then, this enzyme gene expression vector is introduced into a suitable microorganism, whereby the microorganism is rendered capable of producing coenzyme $Q_{10}$. The host microorganism is not particularly restricted but *Escherichia coli* can be used with advantage. The *Escherichia coli* is not particularly restricted but includes such strains as XL1-Blue, BL-21, JM109, NM522, DH5α, HB101 and DH5, among others. Among these, *E. coli* DH5α can be used with particular advantage. For example, when the expression vector pNTSal containing the decaprenyl diphosphate synthase gene is introduced into this *E. coli* strain, the coenzyme $Q_{10}$, which the intact *E. coli* inherently does not produce, can be produced in a large amount. This *E. coli* DH5α (pNTSal) has been deposited with National Institute of Bioscience and Human-Technology (Higashi 1-1-3, Tsukuba-shi, Ibaraki, Japan) under the accession number of FERM BP-6844.

Furthermore, *Escherichia coli* KO229 (Journal of Bacteriology, 179, 3058–3060 (1997), the octaprenyl diphosphate synthase gene-knockout *E. coli* strain constructed by Kawamukai et al. as the host microorganism, is incapable of producing coenzyme $Q_8$ and can be utilized as the host for higher production of coenzyme $Q_{10}$.

The gene can be used not only singly but may be introduced together with another biosynthesis-related gene into a microorganism to thereby obtain still more satisfactory results.

Coenzyme $Q_{10}$ can be produced by culturing the transformant obtained according to the invention and harvesting the product coenzyme $Q_{10}$ in a per se known manner. When the host microorganism is a strain of *Escherichia coli*, either LB broth or M9 broth containing glucose and casamino acids can be used as the culture broth. In order that the promoter may be allowed to function with efficiency, the broth may be supplemented with ascertain chemical such as isopropyl-thiogalactoside or indolyl-3-acrylic acid. Culture can be carried out at 37° C. for 17 to 24 hours, for instance, optionally under aeration or agitation. In the practice of the invention, the product coenzyme $Q_{10}$ may be used after purification or as it is in the crude form, depending on the intended use. Isolation of coenzyme $Q_{10}$ from the culture can be made by using known separation and purification procedures in a suitable combination. As such known separation and purification procedures, there can be mentioned techniques utilizing solubilities, such as salting-out and solvent precipitation; techniques chiefly utilizing differences in molecular weight, such as dialysis, ultrafiltration, gel filtration and (SDS-)polyacrylamide gel electrophoresis; techniques utilizing differences in charge, such as ion exchange chromatography; techniques utilizing specific affinity, such as affinity chromatography; techniques utilizing differences in hydrophobicity, such as reversed-phase high performance liquid chromatography; and techniques utilizing differences in isoelectric point, such as isoelectric focusing, among others.

The use for the coenzyme $Q_{10}$ obtained according to the invention is not particularly restricted but the enzyme can be applied to pharmaceuticals with advantage.

BEST MODE FOR CARRYING OUT THE INVENTION

EXAMPLE 1

Figure 1:
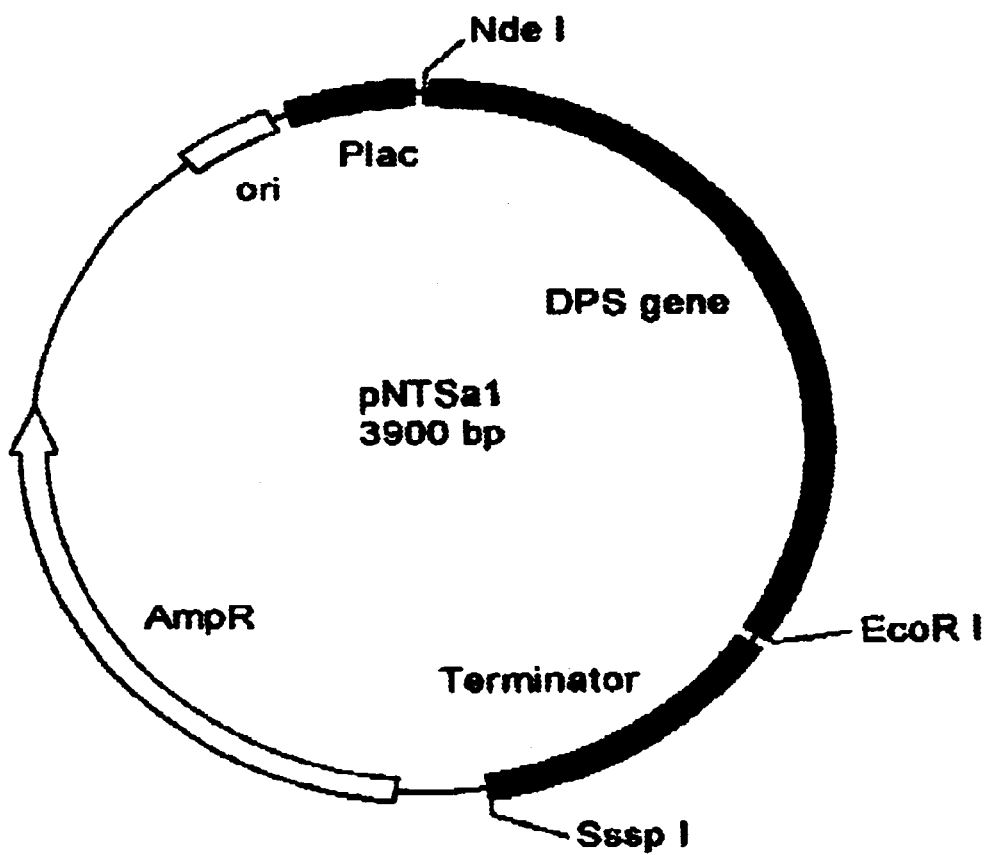
FIG. 1 is a restriction map of the pNTSal vector containing the decaprenyl diphosphate synthase gene.

The chromosome DNA of *Saitoella complicata* IFO 10748 was prepared by the method of C. S. Hoffman et al. (Gene, 57 (1987), 267–292). Based on the homology to the known long-chain prenyl diphosphate synthase genes, PCR primers, i.e. DPS-1 (SEQ ID NO:3) and DPS-1 1AS (SEQ ID NO:4), were designed. In the above-sequences, R stands for A or G; Y for C or T; and N for G, A, T or C. Using these primers, PCR was carried out under the conditions of heat treatment at 94° C., 3 min. followed by 40 cycles of 94° C., 1 min.→43° C., 2 min.→72° C., 2 min., and the PCR product was analyzed by 1.2% agarose gel electrophoresis.

The ca 220 bp fragment thus obtained was excised from the gel and purified using a DNA extraction kit (Sephaglas™ BrandPrep Kit, Amersham Pharmacia Biotech). Then, using a PCR product direct cloning kit (pT7BlueT-Vector Kit, NOVAGEN), the DNA was cloned into the *E. coli* expression vector to give pT7-SaDPS. Then, using a DNA sequencer (Model 377, Perkin-Elmer) and a DNA sequencing kit (Perkin-Elmer; ABI PRISM™ BigDye™ Terminator Cycle Sequence Ready Reaction Kit with AmptiTaq™ DNA Polyrnerase, FS), DNA sequencing was carried out according to the kit manufacturer's protocol. As a result, there was obtained a sequence corresponding to the nucleotides 717 through 924 of SEQ ID NO:1. The translation sequence thus obtained contained the sequence of SEQ ID NO: 9, which is a characteristic region of polyprenyl diphosphate synthases and, therefore, was considered to be part of the decaprenyl diphosphate synthase gene.

EXAMPLE 2

Using 0.03 µg of a pT7-SaDPS vector containing a 220 bp DNA fragment which was considered to be the decaprenyl diphosphate synthase gene of *Saitoella complicata* IFO 10748, PCR using primers Sa-1S (which has the sequence of SEQ ID NO:5) and Sa-2As (which has the sequence of SEQ ID NO:6) was carried out. The PCR product was subjected to gel electrophoresis using 1.2% agarose (Takara) and a ca 145 bp fragment was excised from the gel and purified using a DNA extraction kit (Sephaglas™ BrandPrep Kit; Amershaam Pharmacia Biotech). Using about 100 ng of this DNA fragment, chemiluminescence labeling was performed using ECL Direct Nucleic Acid Labeling System (amersham Pharmacia Biotech).

EXAMPLE 3

The chromosome DNA of *Saitoella complicata* IFO 10748 was digested with the restriction enzyme EcoRI and electrophoresed through 0.8% agarose gel. This gel was denatured with alkali (0.5 M NaOH, 1.5 M NaCl) and neutralized (0.5 M Tris-HCl (pH 7.5), 1.5 M NaCl), after which HYBOND N+ filter (Amersham) was placed on the gel and the Southern transfer was carried out using 20×SSC overnight. This filter was dried and heated at 80° C. for 2 hours and using ECL Direct Nucleic Acid Labeling/Detection System (Amersham Pharmacia Biotech), Southern hybridization and detection were carried out. Thus, using Gold Hybridization Solution (Amercham Pharmacia Biotech), prehybridization was performed at 42° C. for 1 hour.

The chemiluminescence-labeled probe was heated at 95° C. for 5 minutes, quenched on ice, and added to the prehybridization solution used for filter prehybridized and the hybridization was carried out at 42° C. for 22 hours. This filter was washed with 0.5×SSC solution containing 6 M urea and 0.4% SDS at 42° C. twice for 20 minutes each and, then, washed with 2×SSC solution at room temperature twice for 5 minutes each. This filter was immersed in Enhanced Chemiluminescence Reagent (product of Amersham Pharmacia Biotech) and, then, exposed in intimate contact with X-ray film to detect a black exposure band.

As a result, the probe was found to have firmly hybridized with a ca. 10 kbp EcoRI restriction fragment.

EXAMPLE 4

The chromosome DNA of *Saitoella complicata* IFO 10748 was digested with the restriction enzyme EcoRI and electrophoresed through 0.8% agarose and a ca. 10 kbp fragment of the DNA was excised from the gel and purified to prepare a DNA fragment for cloning. Using λ-DASHII Phage Kit (product of Stratagene), the above DNA fragment was inserted into the EcoRI site of its phage and the packaging was made using In Vitro Packaging Kit (Amersham). *Escherichia coli* XL1-Blue MRA (P2) was infected and layered on NZY plate medium (5 g/L NaCl, 2 g/L MgSO$_4$.7H$_2$O, 5 g/L yeast extract, 10 g/L NZ amine, 18 g/L agar (pH 7.5)) together with NZY soft agar (the agar only of NZY plate medium, 8 g/L) for use as a plaque. This was transferred to HYBOND N+ filter (product of Amersham), denatured with alkali (0.5 M NaOH, 1.5 M NaCl), neutralized (0.5 M Tris-HCl (pH 7.5), 1.5 M NaCl), dried, and heated at 80° C. for 2 hours.

Using 9 filters heated as above, the prehybridization and the hybridization using the chemiluminescence-labeled probe were carried out as in Example 3 and the filters were rinsed. Each filter was then dried and exposed in intimate contact with X-ray film and the phage plaque corresponding to the black exposure spot was separated. The phage of the separated plaque was used to infect *E. coli* in the same manner as above and transferred to the filter and the hybridization was carried out again for confirmation. As a result, 6 phage clones could be selected.

Using a suspension of the phage, PCR was carried out using said Sa-1S and Sa-2AS primers, and as a result, a 145-bp DNA fragment could be detected in 6 clones. Therefore, the phage DNA was prepared from the recombinant λ-DASHII phage particles according to Laboratory Manual for Genetic Engineering (Masami Muramatsu, Maruzen, 1990). For subcloning, the phage DNA thus prepared was digested with the restriction enzymes SalI and SacI and electrophoresed through 0.8% agarose gel. This gel was denatured with alkali (0.5 M NaOH, 1.5 M NaCl) and neutralized (0.5 M Tris-HCl (pH 7.5), 1.5 M NaCl). Then, a HYBOND N+ filter (Amersham) was placed on the gel and subjected to Southern transfer using 20×SSC overnight. This filter was dried and heated at 80° C. for 2 hours, after which the Southern hybridization and detection were carried out using ECL Direct Nucleic Acid Labeling/Detection System (Amersham Pharmacia Biotech). Thus, using Gold Hybridization Solution (Amersham Pharmacia Biotech), the prehybridization was carried out at 42° C. for 1 hour.

The chemiluminescence-labeled probe was heated at 95° C. for 5 minutes, quenched on ice, and added to the prehybridization solution used for filter prehybridized and the hybridization was carried out at 42° C. for 22 hours. This filter was washed with 0.5×SSC containing 6 M urea and 0.4% SDS at 42° C. twice for 20 minutes each and, then, with 2×SSC at room temperature twice for 5 minutes each. The filter was immersed in Enhanced Chemiluminescence Reagent (Amersham Pharmacia Biotech) and exposed in intimate contact with X-ray film to detect a black exposure band.

As a result, the probe was found to have intimately hybridized with a ca. 4.5 kb fragment as obtained by digestion with the restriction enzyme SalI and a ca. 3.5 kb fragment as obtained by digestion with SacI.

The phage DNA was digested with the restriction enzymes SalI and SacI and electrophoresed through 0.8% agarose gel. The restriction fragment corresponding to the position and size of the black exposure band was excised from the gel and purified using a DNA extraction kit (Sephaglas™ Brand Prep Kit; Amersham Pharmacia Biotech). Then, using a DNA sequencer (Model 377, Perkin-Elmer Corp.) and a DNA sequence kit (Perkin-Elmer Corp., ABI PRISM™ BigDye™ Terminator Cycle Sequence Ready Reaction Kit with AmpliTaq™ DNA polymerase, FS), the sequencing was carried out in accordance with the manufacturer's protocol.

As a result, it was found that the SalI site and SacI site are located at positions 1124 and 1241, respectively, of SEQ ID NO:1 and that neither fragment contained the C-terminal. So, for SalI, which is the upstream one of the two restriction enzymes, in the decaprenyl diphosphate synthase gene, the remaining fragments were examined. As a result, a 3 kbp fragment was found to contain a sequence including a terminal region of the SacI fragment up to the termination codon. By analyzing these 3 restriction fragments, the full-length sequence of the decaprenyl diphosphate synthase gene could be elucidated. Of the three DNA fragments, the ca 1.6 kbp fragment was sequenced. The result is shown as SEQ ID NO:1. Moreover, the amino acid sequence deduced from the above DNA sequence is shown as SEQ ID NO:2.

Comparison of the DNA sequence thus obtained with that of the decaprenyl diphosphate synthase gene of *Saccharomyces cerevisiae* as described in Journal of Biological Chemistry, 265, 13157–13164 (1990) revealed about 48% homology on the amino acid level as analyzed using Hitachi Soft Engineering's DNASIS software. Comparison with the decaprenyl diphosphate synthase derived from *Schizosaccharomyces pombe* as described in Japanese Kokai Publication Hei-9-173076 by means of DNASIS revealed 49% homology on the amino acid level.

EXAMPLE 5

In order to selectively excise the gene region coding for decaprenyl diphosphate synthase from the prepared phage DNA, PCR was carried out using synthetic DNA primers Sa-N1 (which has the sequence of SEQ ID NO:7) and Sa-C (which has the sequence of SEQ ID NO:8) in otherwise the same manner as in Example 3. After digestion with the restriction enzymes NdeI and EcoRI, the fragment was inserted into the expression vector pUCNT (disclosed in Example 12(1) of U.S. Pat. No. 6,083,752, which is equivalent to WO 94/03613) to construct the decaprenyl diphosphate synthase gene expression vector pNTSal. The restriction map of the expression vector pNTSal thus obtained is shown in FIG. 1. It is to be noted that DPS represents the coding region of the decaprenyl diphosphate synthase gene.

EXAMPLE 6

The decaprenyl diphosphate synthase gene expression vector pNTSal constructed as above was introduced into *Escherichia coli* DH5α. The microorganism was shake-cultured in 10 mL of LB both at 37° C. overnight and the cells were harvested by centrifugation (3000 rpm, 20 min.).

Figure 2:
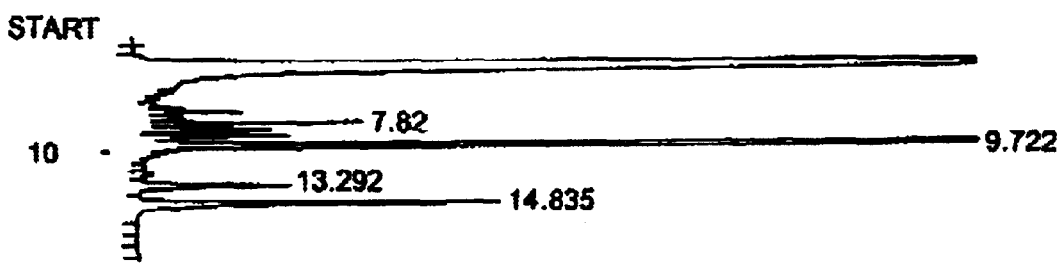
FIG. 2 is an HPLC chart of the coenzyme $Q_{10}$ produced by the recombinant *Escherichia coli* DH5α as transformed with the decaprenyl diphosphate synthase gene.
Figure 2:
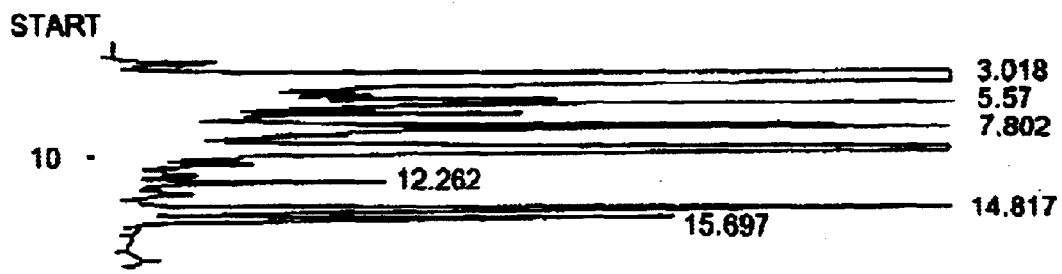
Figure 2:
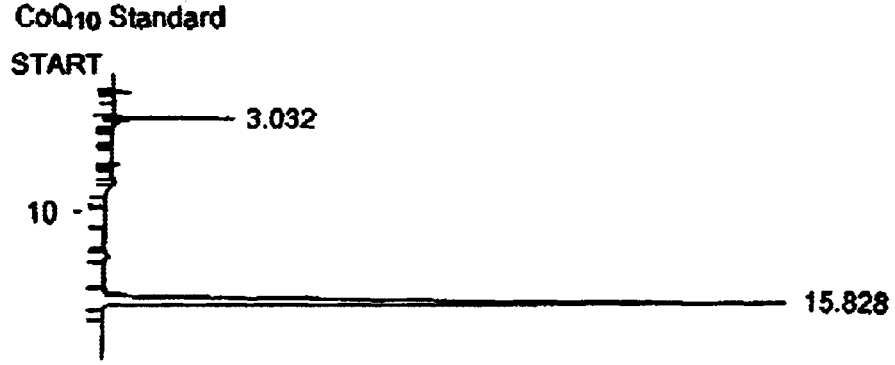

The cells were suspended in 1 mL of 3% aqueous solution of sulfuric acid and heat-treated at 120° C. for 30 minutes. Then, 2 mL of 14% aqueous solution of sodium hydroxide was added and the mixture was further heat-treated at 120° C. for 15 minutes. The lysate obtained was extracted with 3 mL of hexane-isopropyl alcohol (10:2), and after centrifugation, 1.5 mL of the organic layer was separated and evaporated to dryness under reduced pressure. The residue was dissolved in 200 μL of ethanol and a 20 μL portion of the solution was subjected to HPLC analysis (LC-10A, Shimadzu Corporation). Fractionation was carried out using a reversed-phase column (YMC-pack ODS-A, 250×4.6 mm, S-5 μm, 120 A) and, as the mobile phase, ethanol-methanol (2:1) and the coenzyme $Q_{10}$ produced was detected from the absorbance at the wavelength of 275 nm. The result is shown in FIG. 2. As can be seen from FIG. 2, it was found that when the decaprenyl diphosphate synthase gene is introduced into a host and allowed to be expressed, the resulting recombinant *Escherichia coli* produces coenzyme $Q_{10}$ which *E. coli* in general inherently does not produce.

The recombinant *E. coli* DH5α (pNTSal) obtained as above has been deposited with National Institute of Bioscience and Human-Technology (Higashi 1-1-3, Tsukuba-shi, Ibaraki, Japan) as of Heisei 11, August 17 (accession number FERM BP-6844)

EXAMPLE 7

The octaprenyl diphosphate synthase gene-knockout *Escherichia coli* KO229 constructed by Kawamukai et al. is known to retain the gene supported on the spectinomycin-resistant plasmid (pKA3) and die on dropout of said plasmid (Journal of Bacteriology, 179, 3058–3060 (1997). The pNT-Sal was introduced into the above knockout strain, culturing the microorganism in 10 mL of ampicillin-containing LB broth by shake culture at 37° C. overnight, subculturing 1% of the culture in 10 mL of fresh ampicillin-containing LB broth and culturing the microorganism further by shake-culture at 37° C. overnight, and after 9 cycles of the above cultural procedure, selecting the strain growing on ampicillin-containing LB plate medium but not growing on pectinomycin-containing LB plate medium.

EXAMPLE 8

The pNTSal-transfected strain constructed in Example 7 was shake-cultured in 10 mL of LB broth at 37° C. overnight and the cells were harvested by centrifugation (3000 rpm, 20 min.).

Figure 3:
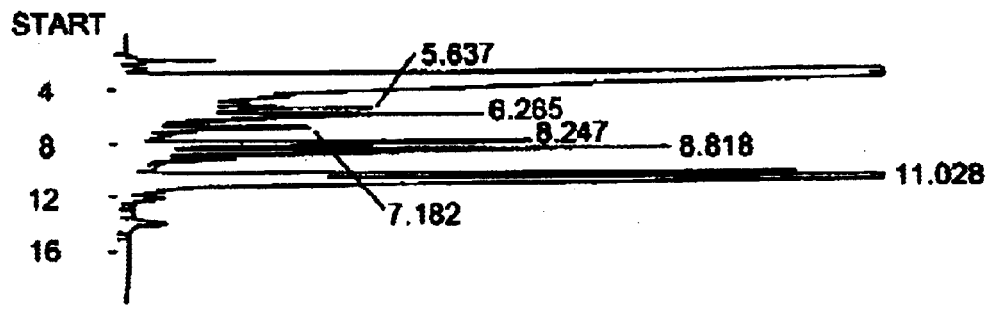
FIG. 3 is an HPLC chart of the coenzyme $Q_{10}$ produced by the recombinant *Escherichia coli* KO229 as transformed with the decaprenyl diphosphate synthase gene.
Figure 3:
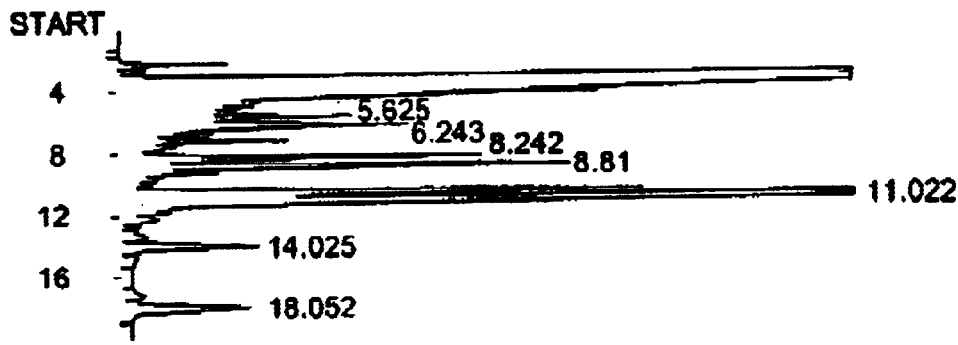
Figure 3:
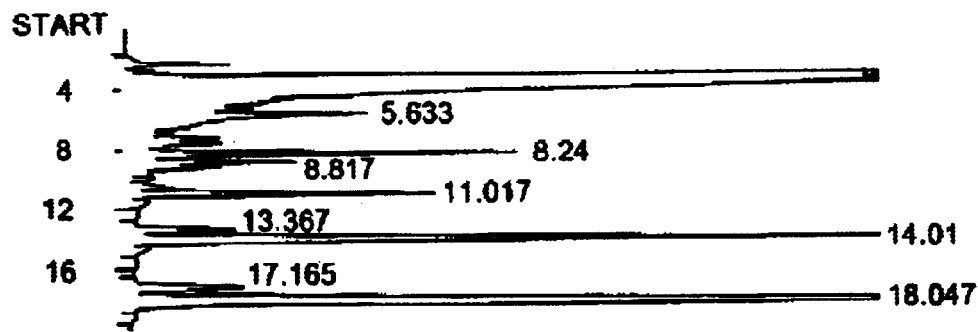
Figure 3:
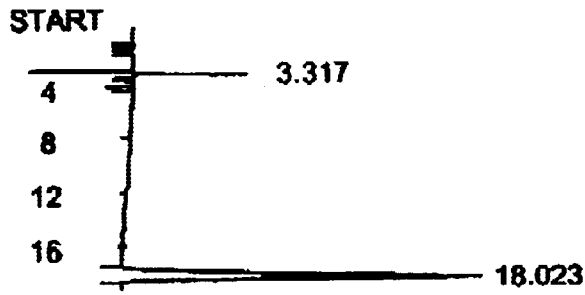

The cells were suspended in 1 mL of 3% aqueous solution of sulfuric acid and heat-treated at 120° C. for 30 min. Then, 2 mL of 14% aqueous solution of sodium hydroxide was added and the mixture was further heat-treated at 120° C. for 15 minutes. The lysate cells were extracted with 3 mL of hexane-isopropyl alcohol (10:2) and centrifuged to recover 15 mL of the organic layer and the solvent was evaporated to dryness under reduced pressure. The residue was dissolved in 200 μL of ethanol and a 20 μL portion of the solution was subjected to HPLC analysis (LC-10A, Shimadzu Corporation). Fractionation was carried out by using a reversed-phase column (YMC-pack ODS-A, 250×4.6 mm, S-5 μm, 120 A) and, as the mobile phase, ethanol-methanol (2:1) and the product coenzyme $Q_{10}$ was detected from the absorbance at the wavelength of 275 nm. The result is shown in FIG. 3. It is clear from FIG. 3 that as the decaprenyl diphosphate synthase gene was introduced and allowed to be expressed, the host *Escherichia coli* was enabled to produce coenzyme $Q_{10}$ which it inherently does not produce and enabled to be transformed so as to yield coenzyme $Q_{10}$ in an increased amount more than that of the coenzyme $Q_{10}$ producer *E. coli* strain.

INDUSTRIAL APPLICABILITY

The gene coding for the key enzyme associated with the biosynthesis of coenzyme $Q_{10}$, namely decaprenyl diphosphate synthase, was isolated from fungi of the genus Saitoella and its nucleotide sequence was elucidated. Furthermore, the gene was successfully introduced and expressed in *Escherichia coli*. By utilizing the technology of the invention, coenzyme $Q_{10}$ in use as a pharmaceutical can be produced with improved efficiency.

What is claimed is:

1. An isolated or purified DNA having the nucleotide sequence shown under SEQ ID NO: 1.

2. An isolated or purified protein having the amino acid sequence shown under SEQ ID NO:2.

3. An isolated or purified DNA coding for the protein according to claim 2.

4. An expression vector comprising the DNA according to claim 1.

5. A transformant as obtainable by transforming a host microorganism with the DNA according to claim 1.

6. A transformant as obtainable by transforming a host microorganism using the expression vector according to claim 4.

7. The transformant according to claim 5 wherein the host microorganism is *Escherichia coli*.

8. The transformant according to claim 7 wherein the *Escherichia coli* is *Escherichia coli* DH5α.

9. The transformant according to claim 10, which is *E. coli* DH5α (pNTSal) (FERM BP-6844).

10. A process for producing a coenzyme $Q_{10}$ which comprises culturing the transformant according to claim 5 in a culture broth and harvesting the coenzyme $Q_{10}$ produced and accumulated in the resulting culture.

11. An expression vector comprising the DNA according to claim 3.

12. A transformant as obtainable by transforming a host microorganism with the DNA according to claim 3.

13. The transformant according to claim 6 wherein the host microorganism is *Escherichia coli*.

14. A process for producing a coenzyme $Q_{10}$ which comprises culturing the transformant according to claim 6 in a culture broth and harvesting the coenzyme $Q_{10}$ produced and accumulated in the resulting culture.

15. A process for producing a coenzyme $Q_{10}$ which comprises culturing the transformant according to claim 7 in a culture broth and harvesting the coenzyme $Q_{10}$ produced and accumulated in the resulting culture.

16. A process for producing a coenzyme, $Q_{10}$ which comprises culturing the transformant according to claim 8 in a culture broth and harvesting the coenzyme $Q_{10}$ produced and accumulated in the resulting culture.

* * * * *